United States Patent [19]

Emmett et al.

[11] Patent Number: 4,750,771

[45] Date of Patent: Jun. 14, 1988

[54] LENS CLEANING AND HANDLING DEVICE

[76] Inventors: Bradley K. Emmett; Paul D. Emmett, both of 132 W. Charlotte Ave., Mount Holly, N.C. 28120

[21] Appl. No.: 16,612

[22] Filed: Feb. 19, 1987

[51] Int. Cl.⁴ .......................... A61F 9/00; G02C 13/00
[52] U.S. Cl. ................................ 294/99.2; 15/104 R; 294/1.2
[58] Field of Search ................. 294/1.2, 2, 64.1, 99.2; 15/104.92–104.94, 214, 104 R; 51/216 LP, 217 L, 229, 284 R; 206/5.1

[56] References Cited

U.S. PATENT DOCUMENTS

| | | | |
|---|---|---|---|
| 2,055,314 | 9/1936 | Seburger | 15/214 X |
| 3,584,908 | 6/1971 | Ray | 294/1.2 |
| 4,126,345 | 11/1978 | List | 294/1.2 |
| 4,221,414 | 9/1980 | Schrier | 294/1.2 |
| 4,223,782 | 9/1980 | Giambalvo | 206/5.1 |
| 4,245,859 | 1/1981 | Rainin | 294/1.2 |
| 4,504,994 | 3/1985 | Johnston | 15/104.92 |
| 4,520,923 | 6/1985 | Waldman | 206/5.1 |
| 4,559,662 | 12/1985 | Kunold | 15/104.92 X |

FOREIGN PATENT DOCUMENTS

| | | | |
|---|---|---|---|
| 2701016 | 7/1978 | Fed. Rep. of Germany | 206/5.1 |
| 1431168 | 4/1976 | United Kingdom | 294/1.2 |

Primary Examiner—Johnny D. Cherry
Attorney, Agent, or Firm—Ralph H. Dougherty

[57] ABSTRACT

Apparatus for handling and cleaning contact lenses comprising a pair of tweezer arms connected at one end and biased apart at the other end, the connected end carrying a contact lens support pad. The free ends of the biased arms may advantageously be provided with removable sleeves for efficient grasping and handling of soft contact lenses.

13 Claims, 1 Drawing Sheet

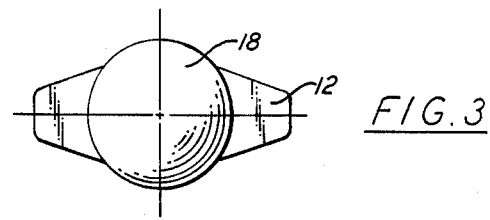
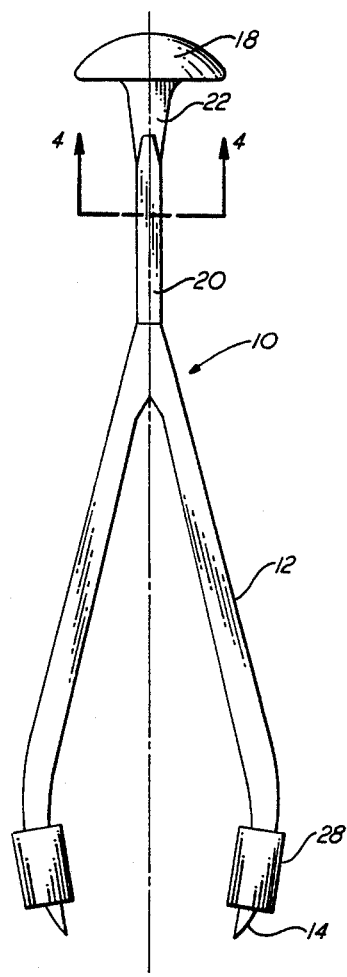
FIG. 1
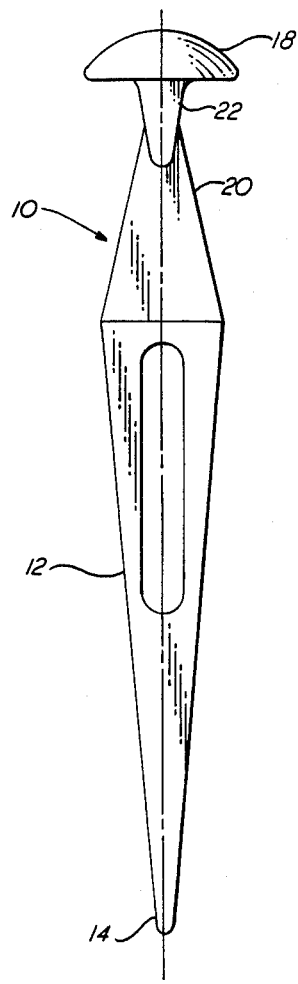
FIG. 2
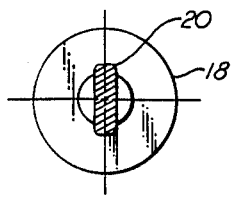
FIG. 4

LENS CLEANING AND HANDLING DEVICE

FIELD OF THE INVENTION

The present invention relates to contact lens handling and cleaning apparatus and particularly to such a device for use with soft type contact lenses.

BACKGROUND OF THE INVENTION

Hard contact lenses were developed prior to 1950 and the market for such lenses has enjoyed a steady growth.

Soft lenses entered the market in the early 1970's and have enjoyed increasing use. Hard lenses are hydrophobic whereas soft lenses are hydrophylic, that is, porous, and thus soft lenses require more finger handling and are more difficult to remove from a lens case as well as to place the lens in the eye. All of this handling requires excessive care and frequent cleaning of the lens by the user.

Contact lenses can be a breeding ground for a bug that can infect the wearer's eyes with pain, irritation, blurred vision or blindness. The acanthamoeba organism thrives in sea water, soil, air-borne dust, and warm, moist environments. Many of these elements can be found in an eye, creating a culture ripe for this organism. If a contact lens wearer does not regularly disinfect or sterilize the lens, acanthamoeba can spawn a bacterial infection known as acanthamoebacaritis, which is often mistaken for a herpes virus or conjunctivitis. The present invention promotes the cleaning of contact lenses on a regular basis, which tends to prevent the development of the acanthamoeba organism and other vision problems.

Conventional cleaning of contact lenses is most commonly accomplished manually by placing a lens in the palm of one hand, applying cleaning solution to the lens and working the cleaning solution into the lens with the finger tip of the other hand. Alternatively, the lens can be applied to a wetted finger tip, the solution applied to the palm of the other hand and the cleaning solution rubbed into the lens by a rubbing motion of the lens-carrying finger tip into the palm. One of the most common problems occurring is the fingernail of the manipulating finger contacting and damaging or tearing the lens during this procedure. It is also possible for the lens to become folded and damaged. Dirt or foreign matter is more commonly carried around fingernails and on fingertips than it is in the palm of the hand, particularly when a cleaning solution is applied to the palm of the hand.

Prior art tweezers hold items by gripping friction or pressure of opposing arms against the object being held.

Many styles of tweezers are known in the art, as exemplified by Kelly U.S. Pat. No. 4,199,180, which illustrates a substantial number of possible tweezer arms, however, Kelly's tweezers or "biased implement holder" have a split resilient ring with sockets for receiving various implements.

Lens cleaning devices are exemplified by Rhue U.S. Pat. No. 4,187,574, which teaches a housing having a scrubbing pad within in it, and an off-set dome, which causes movement of the lens within the cleansing apparatus. Mencke U.S. Pat. No. 4,533,399 teaches a method for cleaning a contact lens wherein a moistened, thermoplastic polymeric fibrous web contacts and rubs a contact lens to remove proteinaceous and particulate matter therefrom.

Ross U.S. Pat. No. 4,082,339 teaches a cup type instrument for insertion and removal of soft contact lenses.

Johnston U.S. Pat. No. 4,504,994 teaches apparatus for cleaning contact lenses in which a handle assembly carries a convex surface and a handle shank for manipulating a contact lens in a concave recessed surface within a body formed of soft, slightly abrasive material. The present invention avoids the abrasive material of the recessed receptacle.

OBJECTS OF THE INVENTION

It is the principal object of the present invention to provide an apparatus for grasping and cleaning soft contact lenses.

It is another object of this invention to provide a small cleaning and grasping apparatus for contact lenses which is of sufficiently small size that a user can conveniently carry it with him at all times.

It is also an object of this invention to provide a contact lens cleaning apparatus which avoids fibrous and abrasive cleansing surfaces.

It is another of this invention to provide a cleaning and grasping apparatus for contact lenses which provide a positive grasp of the lens.

BRIEF SUMMARY OF THE INVENTION

The present apparatus includes a convex end or surface for engaging a contact lens. It is recognized that contact lens wearers resist carrying any more cleaning apparatus than the absolute minimum necessary. Thus, the present invention is adapted for use with a cleaning solution to be placed in the palm of one hand of the contact lens wearer. The other end of the invented apparatus includes a tweezer in which biased elastic arms are provided for engaging and lifting or moving a lens.

BRIEF DESCRIPTION OF THE DRAWINGS

The present invention is better understood by referring to the following detailed description of the preferred embodiment and the appended drawings, in which;

FIG. 1 is a front elevational view of the invented contact lens cleaner and holder.

FIG. 2 is a side view of the invented contact lens cleaner and holder.

FIG. 3 is a top view of the invented contact lens cleaner and holder.

FIG. 4 is a horizontal sectional view of the invented contact lens cleaner and holder taken along the line 4—4 of FIG. 1.

DETAILED DESCRIPTION

Referring now to FIG. 1, which shows the preferred embodiment of our invention, the invented apparatus 10 is a unitized device having a pair of downwardly extending arms 12 connected at their upper ends, the free ends 14 preferably being tapered to a point or nearly so. Fixed to and integral with the upper end of the apparatus 10 is a convex cleaning head or convex contact lens support pad 18. Advantageously, the convex surface of the contact lens support pad is a spherical segment, or a partially spherical segment. Between the lens support pad 18 and the biased arms 12 is a connector 20, which provides a finger grip for the user. The connector 20 is preferably flat, tapering toward a tapered lens support pad support 22, which support 22 has a rounded, or circular cross-section.

A tubular sleeve 28 may be affixed to each tip or free end 14 of arms 12. The arms are preferably wider than they are thick, and taper from the widest point of their upper extremity to the narrowest point of their lower extremity. The arms also preferably bend or curve inwardly for from one-tenth to one-third of their length at their lower portion as shown in FIG. 1. The sleeves 28 preferably are affixed only to this lowermost portion of the arms. The tips of the arms may protrude through the sleeves, to such extent as desired by the user.

The material from which the invented apparatus is made must be properly selected to minimize the possibility of damaging a contact lens. The material must have good resiliency and must return to its original configuration upon release of force thereon. Preferred resilient plastic materials are: terpolymers, thermoplastics, elastomers, or any combination of these. Especially well suited materials are polypropylene elastomers, polyisoprene elastomers, and silicon elastomers.

The tweezer portion consists of a pair of arms connected at one end and biased into an open position at the other end to create a void between them. The arms may be straight or curved, but preferably have a short curved section near the free or open ends. The end of the apparatus opposite the free ends of the arms carries a convex lens-engaging surface, or anvil, shaped to mate with the concave surface of a contact lens. The convex surface supports the lens and is used to manipulate it against the palm of the user while the outer or front surface of the lens is being cleaned.

The present invention is intended for use by placing the contact lens cleaner in the wearer's hand, placing the contact lens on the convex surface of the invented apparatus and rubbing the lens into the palm of the user to effect proper cleaning.

Resilient sleeves, which can be made of a rubberized soft plastic or other resilient material, such as rubber-coated plastic, vinyl or nylon, elastomers, thermoplastics, or terpolymers, are adapted for placement over the tapered ends of the biased arms to provide a positive gripping surface.

In operation, the cleansing solution is placed in the palm of the user's hand, a soft contact lens is picked up by grasping with the resilient sleeves at the ends of the arms, placing the lens in the solution in the wearer's palm and engaging the lens with the convex surface at the end of the apparatus opposite the resilient sleeves.

SUMMARY OF THE ACHIEVEMENTS OF THE OBJECTS OF THE INVENTION

From the foregoing, it is readily apparent that we have provided an apparatus for grasping and cleaning soft contact lenses, in particular, a small cleaning and grasping apparatus for contact lenses which is of sufficiently small size that a user can conveniently carry it with him at all times; and which provides a positive grasp of the lens.

While in accordance with the patent statutes, the best mode or preferred embodiment has been shown and described, it is readily apparent that modifications may be made without departing from the spirit of the invention. Therefore, no limitations are to be inferred except as specifically set forth in the appended claims.

What is claimed is:

1. Apparatus for handling and cleaning contact lenses comprising a pair of biased arms connected at one end and spaced and free at the other end, the free ends being biased apart, the free ends of the biased arms being symmetrically tapered, and a convex contact lens support pad being carried by the connected end.

2. Apparatus according to claim 1 wherein the free ends of the biased arms are turned inwardly over no more than one-third of their length nearer the free ends.

3. Apparatus according to claim 1 wherein the surface of said convex contact lens support pad is a spherical segment.

4. Apparatus according to claim 1 further comprising a finger grip between the convex contact lens support pad and the biased arms.

5. Apparatus according to claim 4 wherein said finger grip comprises a flat surface connecting the connected arms to the contact lens support pad, and is integral with both said arms and said support pad.

6. Apparatus according to claim 1 further comprising removable tubular sleeves adapted to engage said biased arms at their free ends.

7. Apparatus according to claim 6 wherein said sleeves are constructed from a resilient material.

8. Apparatus according to claim 7 wherein said sleeves are rubberized soft plastic.

9. Apparatus according to claim 7 wherein said resilient material is selected from the group comprising elastomers, thermoplastics, and terpolymers.

10. Apparatus according to claim 1 wherein said apparatus is constructed from a resilient material.

11. Apparatus according to claim 10 wherein said material is resilient plastic.

12. Apparatus according to claim 11 wherein said material is selected from the group comprising: terpolymers, thermoplastics, and elastomers.

13. Apparatus according to claim 12 wherein said material is an elastomer selected from the group comprising: polypropylene elastomers, polyisoprene elastomers, and silicon elastomers.

* * * * *